United States Patent [19]

Holland

[11] Patent Number: 5,070,567
[45] Date of Patent: Dec. 10, 1991

[54] ELECTRICALLY-DRIVEN BRUSH

[76] Inventor: Neta Holland, 16 Hana Senesh Street, Herzliya, Israel

[21] Appl. No.: 657,382

[22] Filed: Feb. 19, 1991

Related U.S. Application Data

[63] Continuation of Ser. No. 482,586, Feb. 21, 1990, abandoned.

[30] Foreign Application Priority Data

Dec. 15, 1989 [IL] Israel ........................................ 92720

[51] Int. Cl.$^5$ .......................... A46B 13/02; A46B 9/04
[52] U.S. Cl. ............................................. 15/28; 74/63
[58] Field of Search .................. 15/28, 29, 49.1, 50.1, 15/23; 51/170 T, 177; 74/63

[56] References Cited

U.S. PATENT DOCUMENTS

| | | | |
|---|---|---|---|
| 2,007,073 | 7/1935 | Clarke | 15/49.1 |
| 2,140,307 | 12/1938 | Belaschk et al. | 15/28 |
| 2,142,933 | 1/1939 | Bickford | 15/49.1 |
| 2,215,031 | 9/1940 | Elmore | 15/28 |
| 3,242,516 | 3/1966 | Cantor | 15/28 |
| 3,775,800 | 12/1973 | Veneziani | 15/28 |
| 4,156,620 | 5/1979 | Clemens | 15/22.1 |
| 4,827,550 | 5/1989 | Graham et al. | 15/22.1 |

FOREIGN PATENT DOCUMENTS 3406112  8/1985  Fed. Rep. of Germany .......... 15/28

Primary Examiner—Edward L. Roberts
Attorney, Agent, or Firm—Benjamin J. Barish

[57] ABSTRACT

A toothbrush includes a brush head having a first group of bristle holders arranged along a substantially straight line and a second group of bristle holders arranged in a circle, all the bristle holders being rotatable about their respective axes.

19 Claims, 2 Drawing Sheets

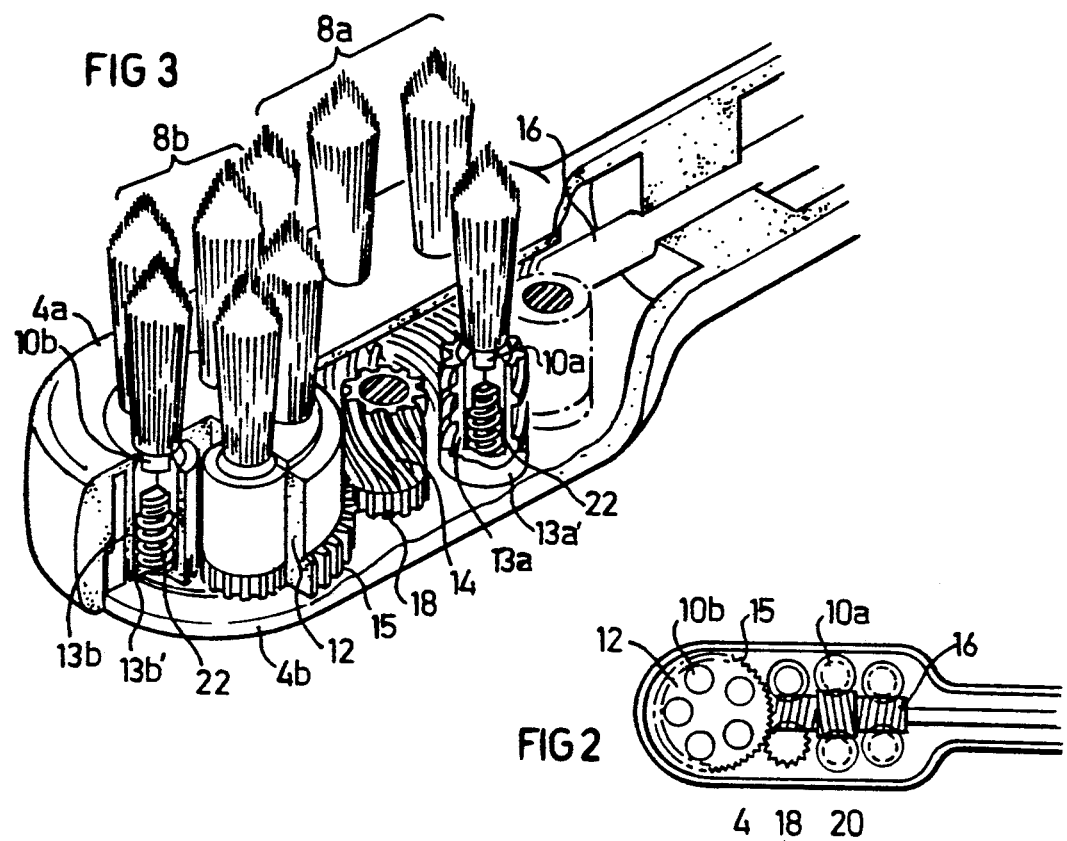
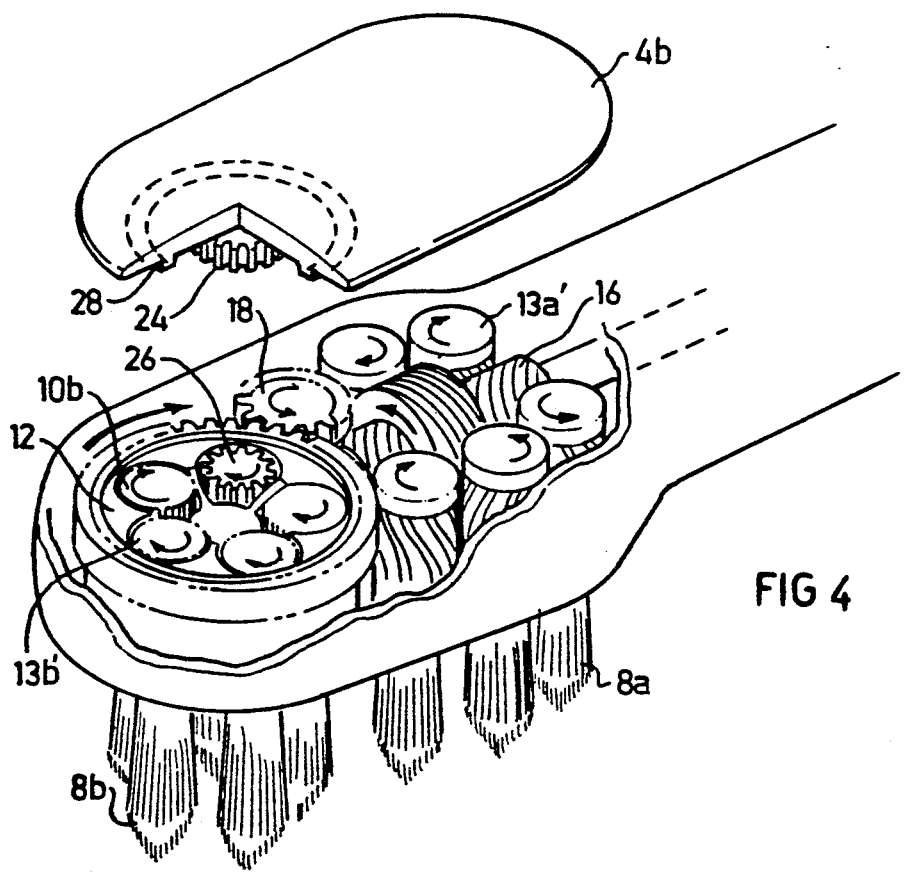

ELECTRICALLY-DRIVEN BRUSH

RELATED APPLICATION

This patent application is a continuation of patent application Ser. No. 07/482,586, filed Feb. 21, 1990, now abandoned.

BACKGROUND OF THE INVENTION

The present invention relates to electrically-driven brushes of the type including a plurality of bristle holders which are driven by an electrical motor contained within the brush. The invention is particularly useful in toothbrushes, and is therefore described below with respect to this application.

A large number of different types of electrically-driven toothbrushes have been developed and are commercially available. Examples of known electrically-driven toothbrushes are described in U.S. Pat. Nos. 3,242,516, 4,156,620, 4,827,550, 4,845,795, 1,947,324, 3,115,652 and 4,274,173. However, efforts are continuously being made to increase the brushing efficiency of such toothbrushes.

OBJECTS AND SUMMARY OF THE INVENTION

An object of the present invention is to provide an electrically-driven brush, and particularly a toothbrush, exhibiting a high degree of brushing efficiency.

According to one aspect of the present invention, there is provided a brush comprising a handle at one end and a brush head at the opposite end. The brush head includes first and second groups of bristle holders. The bristle holders of the first group are disposed in at least one substantially straight line and each is rotatable about its respective axis; while the bristle holders of the second group are dispose din a circle and each is rotatable about its respective axis. An electric motor in the handle includes transmission means within the handle rotates all the bristle holders about their respective rotary axes.

According to another aspect of the present invention, there is provided a toothbrush comprising a handle at one end and a brush head fixed to the handle at the opposite end of the toothbrush. The brush head includes a group of bristle holders disposed in a circle with each rotatable about its respective axis. An electric motor is disposed within the handle, and transmission means extends from the motor in the handle to the bristle holders in the brush head for rotating all the bristle holders about their respective rotary axes.

According to a still further aspect of the present invention, there is provided a brush comprising a handle at one end and a brush head at the opposite end. The brush head includes a group of bristle holders disposed in two substantially straight lines with each bristle holder being rotatable about its respective axis. The device further includes an electric motor in the handle, and transmission means within the brush head and connected to the motor and to the bristle holders for rotating all the bristle holders about their respective rotary axes. The transmission means includes a rotary lead screw coupled to the bristle holders to rotate them during the rotation of the lead screw. The bristle holders of the two lines are formed with threads meshing with the threads of the lead screw; and the lead screw has alternating left-hand and right-hand threads to alternate the directions of rotations of adjacent bristle holders.

An electrically-driven brush constructed in accordance with the foregoing features exhibits a high degree of brushing efficiency and is particularly useful in a toothbrush.

Further features and advantages of the invention will be apparent from the description below.

BRIEF DESCRIPTION OF THE DRAWINGS

The invention is herein described, by way of example only, with reference to the accompanying drawings, wherein:

FIG. 2 is a top plan view illustrating the two groups of bristle holders in the toothbrush of FIG. 1;

FIG. 3 is an enlarged fragmentary view from one side of the brush head of FIG. 1; and FIG. 4 is an enlarged fragmentary view of the opposite side of the brush head of FIG. 1.

DESCRIPTION OF A PREFERRED EMBODIMENT

Figure 1:
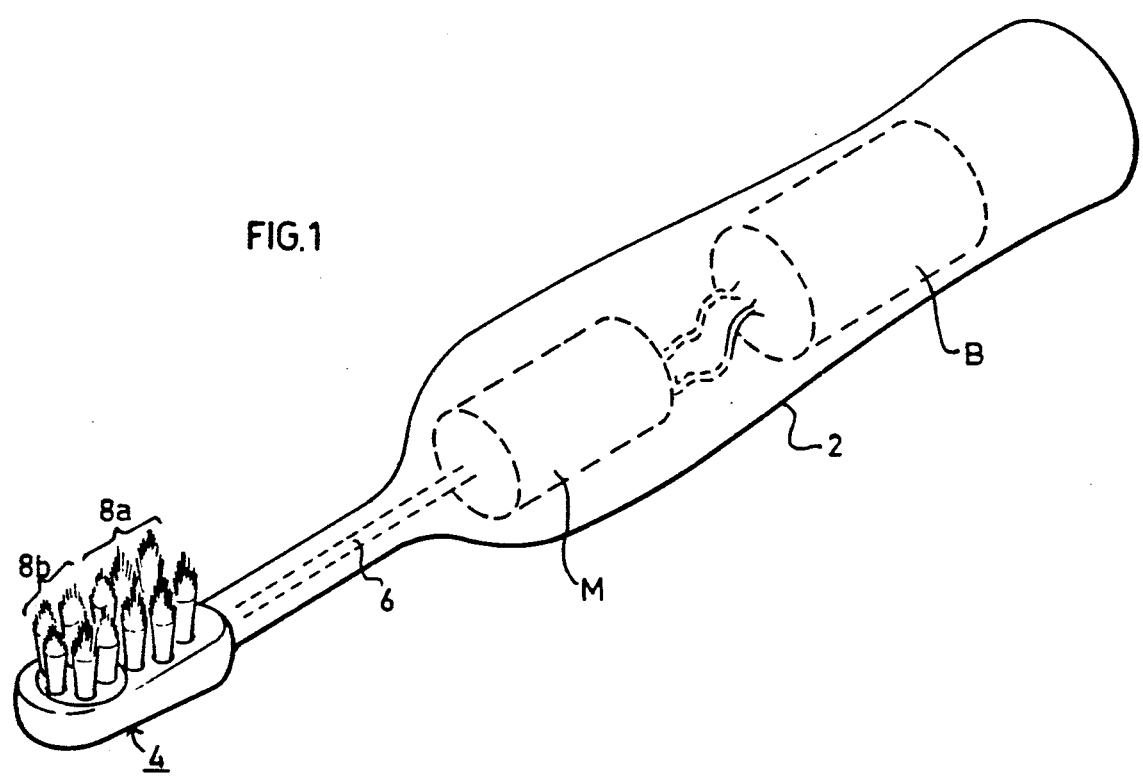
FIG. 1 is a three-dimensional view illustrating one form of toothbrush constructed in accordance with the present invention.

The toothbrush illustrated in the drawings comprises a handle 2 at one end and a brush head 4 at the opposite end connected by a stem 6. Brush head 4 includes two groups of bristles 8a, 8b, carried by respective bristle holders 10a, 10b rotatably mounted in the brush head. As shown particularly in FIG. 2, one group of bristle holders 10a are disposed in two substantially straight parallel lines with each bristle holder being rotatable about its respective axis, whereas the second group of bristle holders 10b, also rotatably mounted about their respective axes, are disposed in a circular array on a rotatable body 12 also rotated about an axis centrally of the rotary axes of the bristle holders 10b.

Handle 2 houses an electrical motor M supplied by a battery B for rotating all the bristle holders 10a, 10b. Motor M drives a transmission, to be described below, which rotates each of the bristle holders 10a about its respective axis, and also rotates body 12 about its respective axis, and each of the second group of bristle holders 10b carried by body 12 about their individual rotary axes. Each of the bristle holders 10a, 10b, is received with a cylindrical sleeve 13a, 13b, closed at one end by an end wall 13a', 13b'. Each sleeve 13a is formed on its outer surface with spiral threads 14. Each sleeve 13b is received within a socket formed in rotatable body 12, which carries a ring gear 15 at its inner end.

The transmission for rotating the two groups of bristle holders 10a, 10b includes a lead screw 16 connected at one end to motor M and meshing at the opposite end with spiral threads 14 of the bristle holder sleeves 10a. The bristle holder sleeve 13a closest to rotatable body 12 is formed with teeth 18 meshing with the teeth of its ring gear 15 so as to rotate that body, and also to individually rotate the bristle holders 10b carried by that body, as will be described more particularly below.

As shown particularly in FIG. 2, there are two substantially straight parallel lines of bristle holders 10a on opposite sides of lead screw 16, with each line including three bristle holders. The spriral threads 14 in the sleeves 13a of the two end pairs of bristle holders 10a mesh directly with the spiral threads of the lead screw 16; whereas the spiral threads 14 in the sleeves 13a of the middle pair of bristle holders 10a mesh with an insert 20 fixed to the lead screw 16 but formed with spiral threads of the opposite hand as compared to the spiral threads on the lead screw. For this purpose, the rotary axes of the middle pair of bristle holders 10a are spaced slightly outwardly from the axes of the two end pairs of bristle holders a sufficient distance to accommodate the insert 20.

As shown particularly in FIG. 3, the bristles 8a, 8b of each group project through openings formed in wall 4a of the brush head 4. In addition, a spring 22 is interposed between each bristle holder 10a, 10b and the end wall of its respective sleeve 13a, 13b for continuously urging the bristle holders outwardly, but permitting them to move inwardly under pressure.

The arrows in FIG. 4 illustrate the direction of rotation of each of the bristle holders 10a, 10b when rotated by lead screw 16. Thus, the rotation of lead screw 16 in one direction will rotate adjacent in-line bristle holders 10a in opposite directions, and will also rotate each pair of bristle holders 10a on the opposite sides of the lead screw in opposite directions.

As shown in FIG. 4, end wall 4b is constructed as a separable cover plate removably attachable to brush head 4 to cover both groups of bristle holders 10a, 10b. Cover plate 4b fixedly carries a gear 24 located to overlie the central axis of rotary body 12 and to mesh with gears 26 carried by each of the bristle holders 10b. The arrangement is such that the rotation of body 12 will cause bristle holders 10b to rotate with that body about the axis of that body, and also to rotate about their individual rotary axes, as shown by the arrows in FIG. 4.

As also shown in FIG. 4, cover plate 4b is formed on its inner surface with a circular rib 28 circumscribing its fixed gear 24 and aligned with the rotary axes of the bristle holders 10b. Rib 28 engages the outer surfaces of the end walls 13b' of the sleeves 13b receiving the bristle holders 10b to space the inner face of the cover plate 4b slightly from the outer faces of the sleeves, and thereby to reduce the friction during the rotation of the bristles.

The toothbrush illustrated in the drawings operates as follows:

Energization of the electrical motor M (e.g., by a switch suitablly located on handle 2, not shown), rotates the lead screw 16. Rotation of the lead screw causes the first group of bristle holders 10a to rotate in the directions of the arrows as illustrated in FIG. 4; the rotatable body 12 carrying the second group of bristle holders 10b will also be rotated, by its ring gear 15 meshing with gear 18 of one of the bristle holders 10a. Rotation of body 12 causes its group of bristle holders 10b also to rotate around the central axis of the body, and the meshing of gears 26 of bristle holders 10b with gear 24 fixed to the cover plate 4b of the brush head, causes each of the bristle holders 10b also to rotate about its respective axis.

While the invention has been described with respect to one preferred embodiment, it will be appreciated that many variations may be made. For example, instead of rotating the bristle holders continuously in one direction about their respective axes, their direction of rotation may be periodically reversed, so that they are actually oscillated about their respective rotary axes. In addition, other transmissions could be used for rotating the bristle holders. Further, the brush could also include a vibrator to vibrate the bristle holders as well as to rotate them. Many other variations, modifications and applications of the invention will be apparent.

What is claimed is:
1. A brush comprising:
   a handle at one end and a brush head at the opposite end;
   said brush head including first and second groups of bristle holders;
   the bristle holders of said first group being disposed in at least one substantially straight line and each being rotatable about its respective axis;
   the bristle holders of said second group being disposed in a circle and each being rotatable about its respective axis;
   and an electric motor in the handle, a transmission means within the had and connected to said motor and to said bristle holders for rotating all the bristle holders about their respective rotary axes.

2. The brush according to claim 1, wherein said bristle holders of the second group are disposed in a circular array on a rotatable body also rotated about an axis centrally of the rotary axes of said second group of bristle holders.

3. The brush according to claim 2, wherein said rotatable body is formed with a circular array of sockets each rotatably receiving one of said bristle holders of the second group.

4. The brush according to claim 3, wherein said transmission means includes a gear carried by each of said bristle holders of the second group, and a fixed gear fixed with respect to said brush head centrally of the rotatable body and meshing with said gears of the bristle holders of the second group.

5. The brush according to claim 4, wherein fixed gear is fixed to a cover plate removably attached to said brush head.

6. The brush according to claim 5, wherein said cover plate is formed with a circular rib circumscribing said fixed gear and aligned with said bristle holders of the second group.

7. The brush according to claim 1, wherein said transmission includes a rotary lead screw coupled to said bristle holders of the first group to rotate them during the rotation of the lead screw.

8. The brush according to claim 7, wherein the bristle holders of said first group are disposed in two lines on opposite sides of said lead screw.

9. The brush according to claim 8, wherein each of said bristle holders of the first group is formed with threads meshing with the threads of said lead screw, said lead screw having alternating left-hand and right-hand threads to alternate the directions of rotation of adjacent bristle holders of the first group.

10. The brush according to claim 1, wherein said bristle holders of the first group are located in two substantially straight parallel lines, and the bristle holders of the second group are located in a rotatable body at one end of said two lines, said transmission means including a lead screw rotating the two lines of bristle holders of the first group, one of the latter bristle holders being coupled to said rotatable body to rotate it and the bristle holders of the second group about their respective rotary axes.

11. A toothbrush comprising:
   a handle at one end and a brush head fixed to the handle at the opposite end of the toothbrush;
   said brush head including a group of bristle holders disposed in a circle and each being rotatable about its respective axis;
   an electric motor disposed within the handle;

and transmission means extending form said motor in the handle to said bristle holders in the brush head for rotating all said bristle holders about their respective rotary axes.

12. The toothbrush according to claim 11, wherein said bristle holders are disposed in a circular array on a rotatable body also rotated about an axis centrally of the rotary axes of said bristle holders.

13. The toothbrush according to claim 12, wherein said rotatable body is formed with a circular array of sockets each rotatably receiving one of said bristle holders.

14. The toothbrush according to claim 13, wherein said transmission means includes a gear carried by each of said bristle holders, and a fixed gear fixed with respect to said brush head centrally of the rotatable body and meshing with said gears of the bristle holders.

15. The toothbrush according to claim 14, wherein said fixed gear is fixed to a cover plate removably attached to said brush head.

16. The toothbrush according to claim 15 wherein said cover plate is formed with a circular rib circumscribing said fixed gear and aligned with said bristle holders for spacing the inner face of the cover plate from said bristle holders.

17. A brush comprising:
a handle at one end and a brush head at the opposite end;
said brush head including a group of bristle holders disposed in two substantially straight lines with each bristle holder being rotatable about its respective axis;
an electric motor in the handle;
and transmission means within the brush head and connected to said motor and to said bristle holders for rotating all said bristle holders about their respective rotary axes;
said transmission means including a rotary lead screw coupled to said bristle holders to rotate them during the rotation of the lead screw;
said bristle holders of the two lines being formed with threads meshing with the threads of said lead screw;
said lead screw having alternating left-hand and right-hand threads to alternate the directions of rotations of adjacent bristle holders.

18. The brush according to claim 17, wherein said bristle holders include two lines of bristle holders on opposite sides of said lead screw.

19. The brush according to claim 17, wherein said brush head includes a second group of bristle holders disposed in a circle and each being rotatable about its respective axis;
one of the bristle holders of said first-mentioned group being coupled to said rotatable body to rotate it and the bristle holders of the second group about their respective rotary axes.

* * * * *